United States Patent [19]

Edens et al.

[11] Patent Number: 5,887,965

[45] Date of Patent: Mar. 30, 1999

[54] COOL WHITE LIGHT SOURCE

[75] Inventors: Roger A. Edens, Oconomowoc; Ronald L. Hueneke, Greendale, both of Wis.

[73] Assignee: Escalon Medical Corp., Skillman, N.J.

[21] Appl. No.: 885,341

[22] Filed: Jun. 20, 1997

Related U.S. Application Data

[63] Continuation-in-part of Ser. No. 732,557, Oct. 15, 1996.

[51] Int. Cl.$^6$ ........................................................ F21V 8/00
[52] U.S. Cl. ............................ 362/32; 362/276; 362/293; 362/804
[58] Field of Search .............................. 362/32, 293, 276, 362/355, 804, 802, 351

[56] References Cited

U.S. PATENT DOCUMENTS

| | | | |
|---|---|---|---|
| 4,082,946 | 4/1978 | Heine et al. | 362/32 |
| 4,385,344 | 5/1983 | Gonser | 362/32 |
| 4,415,952 | 11/1983 | Hattori et al. | 362/32 |
| 4,757,426 | 7/1988 | Scheller et al. | 362/20 |
| 4,855,875 | 8/1989 | Onose et al. | 362/32 |
| 4,870,952 | 10/1989 | Martinez | 128/23 |
| 5,003,434 | 3/1991 | Gonser et al. | 362/32 |
| 5,497,295 | 3/1996 | Gehly | 362/32 |
| 5,513,286 | 4/1996 | Easley | 385/19 |

OTHER PUBLICATIONS

Light Hazards Task Group of the International Standards Organization (ISO) Technical Subcommittee TC–172 SC 7 WG6 for Optical Instruments and the Operating Microscope Subcommittee of the American National Standards Institute Accredited committee Z 80 DRAFT (Sep. 10, 1996), "ISO Standard for Endoilluminators—Fundamental Requirements and Test Methods for Optical Radiation Safety", (pp. 1–16).

*Primary Examiner*—Stephen Husar
*Attorney, Agent, or Firm*—Panitch, Schwarze, Jacobs & Nadel, P.C.

[57] ABSTRACT

A cool white light source for use by surgeons delivers a balanced white light having a color temperature over 500° K. essentially without any halos, rings or darkened regions. The light source includes an electrical circuit for detecting the delivery of radiation toxic to human tissue. If the light source detects the delivery of such toxic radiation, the light generating source is disabled.

30 Claims, 4 Drawing Sheets

COOL WHITE LIGHT SOURCE

CROSS-REFERENCE TO RELATED APPLICATIONS

This application is a continuation-in-part of U.S. patent application Ser. No. 08/732,557 filed Oct. 15, 1996.

BACKGROUND OF THE INVENTION

The present invention relates generally to light sources and, more particularly, to apparatus for providing light which is non-toxic to human eyes.

In order to perform ophthalmic surgery, adequate illumination of the eye is required. Such illumination is not adequately provided by a focused lamp located above the surgical area because the surgical field is within the eye. Rather, a beam of light is usually delivered to the surgical area with a fiber optic cable.

The quality of the light delivered to the surgical area is very important. In order to provide high clarity and vision in an anterior or posterior segment of the eye, it is preferred to deliver a bright, white light to the surgical area. The white light preferably does not include any hues which could make it difficult to distinguish areas within the eye. Typical light sources used in ophthalmic surgery have a correlated color temperature of about 3200° K (Kelvin). In contrast, sunlight, the standard for white light, has a color temperature of about 6800° K. Such low color temperature lamps are used to avoid light toxicity to the eye. However, such low color temperature lamps do not provide a balanced white light, but rather the light includes red, orange or even yellow hues. The inclusion of such hues makes it difficult to view the retinal surface because a high percentage of the surface area of the retina is red. A light which includes a red hue brings out the red tissue of the skin, thereby making it harder to see subtle differences inside the eye. That is, visibility of the natural colors of the illuminated tissue is important for diagnostic purposes, and a color tinted light exacerbates the surgeon's ability to see the work area. Accordingly, it would be desirable to deliver a safe white light to a surgical area of the eye.

Unfortunately, it is difficult to deliver light without any darkened regions and/or dark rings. Thus, it would also be advantageous to deliver the light with a uniform or homogeneous distribution.

BRIEF SUMMARY OF THE INVENTION

Briefly stated, the invention is a white light source for use by surgeons for illuminating an observation area and providing high clarity and vision thereof. The white light source comprises a source generating light having an ultraviolet (UV) spectrum component, an infrared (IR) spectrum component and a substantially continuous spectral distribution of visible light; a first radiation filter for removing at least essentially all of the UV spectrum component of the generated light; a second radiation filter for removing at least substantially all of the IR spectrum component of the generated light toxic to human eye tissue; and means for diffusing the filtered light to facilitate delivering a homogeneous light output.

The invention further comprises a white light source for use by surgeons for illuminating an observation area in a human eye and providing high clarity and vision thereof comprising a source generating light having an ultraviolet (UV) spectrum component, an infrared (IR) spectrum component and a substantially continuous spectral distribution of visible light and a color temperature greater than 3500° K; a first radiation filter located to receive the light generated by the source and remove essentially all of the UV spectrum component of the generated light toxic to human eye tissue; a second radiation filter located to also receive the generated light received by the first radiation filter and remove essentially all of the IR spectrum component of the generated light toxic to human eye tissue, such that the light filtered by the first and second filters is essentially non-toxic to human eye tissue and has a color temperature of greater than 3500° Kelvin; and an electrical circuit for detecting radiation toxic to human eye tissue not filtered by the first and second filters.

The invention further comprises a method of providing a white light for illuminating an anterior or posterior segment of an eye and providing high clarity and vision thereof, comprising the steps of generating light having a continuous light spectrum and color temperature of greater than 3500° K with a light source; filtering ultraviolet (UV) radiation from the generated light with a first filter; filtering infrared (IR) radiation from the generated light with a second filter; diffusing the filtered light; and delivering the diffused, filtered light to a surgical area, wherein the first and second filters do not substantially change the color temperature of the generated light, and the delivered filtered light is at least essentially non-toxic to human eye tissue, has a color temperature of greater than about 3500° K, and is substantially homogeneous in distribution.

BRIEF DESCRIPTION OF THE SEVERAL VIEWS OF THE DRAWINGS

The foregoing summary, as well as the following detailed description of preferred embodiments of the invention will be better understood when in conjunction with the appended drawings. For the purpose of illustrating the invention, there is shown diagrammatically in the drawings, embodiments which are presently preferred as well as other alternate embodiments. It should be understood, however, that the invention is not limited to the specific methods and instrumentalities disclosed. In the drawings.

DETAILED DESCRIPTION OF THE INVENTION

Certain terminology is used in the following description for convenience only and is not limiting. The words "top", "bottom", "lower" and "upper" designate directions in the drawings to which reference is made. The terminology includes the words above specifically mentioned, derivatives thereof and words of similar import.

Figure 1:
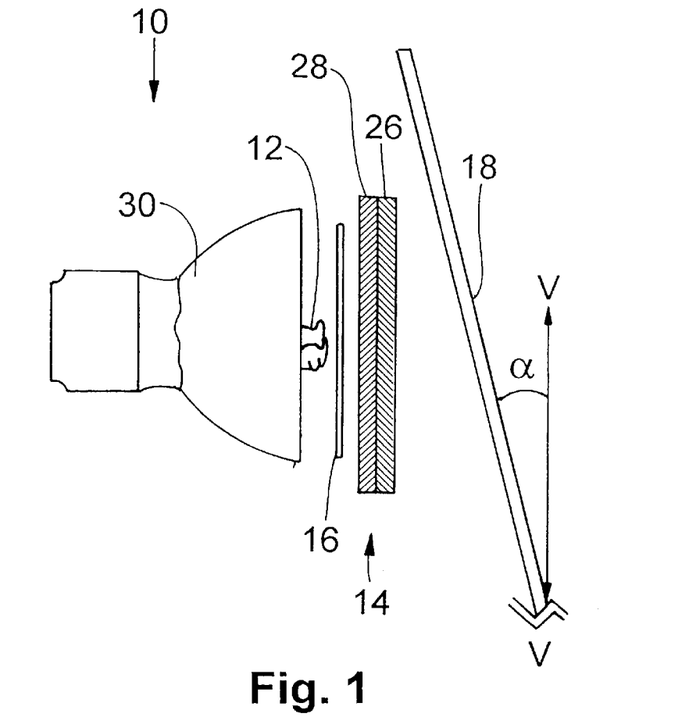
FIG. 1 is a partial side sectional view of a white light source in accordance with the present invention.

Referring to the drawings, wherein like numerals are used for like elements throughout the several figures, there is shown in FIG. 1 an exploded side view of a white light source 10 in accordance with the present invention. The white light source 10 is advantageously used by ophthalmic surgeons for illuminating an anterior or posterior segment of an eye and providing high clarity and vision thereof. The white light source 10 comprises a source 12 which generates light, a filter system 14 for filtering predetermined spectral bands of radiation from the generated light, a diaphragm 16 for controlling transmission of the generated light, and a front panel 18 for facilitating delivery of the light to an area under observation, such as the anterior or posterior portion of an eye.

In order to perform microsurgery on portions of the eye, it is advantageous to deliver a balanced white light which does not contain any red, orange, or yellow hues. The delivered light must also be non-toxic to the eye. The purpose of the source of light 12 is to provide the best possible, near "daylight", illumination. Preferably the source of light 12 generates a substantially continuous spectral distribution of light in the spectral range having wavelengths at least between about 360 nm (nanometers) and about 800 nm. The correlated color temperature of the generated light should be at least 4500° K before filtering if it is to provide improvement over existing sources having 3200° K temperatures. In the presently preferred embodiment, the source of light 12 comprises a high intensity discharge lamp, such as a metal halide short arc lamp, which generates a relatively clear white light with a color temperature of about 5830° K. Such a lamp is generally commercially available For instance, Welch Allyn of Skaneateles Falls, N.Y. supplies metal halide lamps, model nos. M24E001, M21E001 and M18E001, which produce a suitable white light with a substantially continuous spectral distribution of visible light and a relatively high color temperature. Although a metal halide lamp is preferred, it will be apparent to those of ordinary skill in the art that other lamps could be used with the present invention which also generate a relatively continuous band of visible light with a high color temperature, such as a tungsten halogen lamp or a xenon arc lamp.

Figure 2:
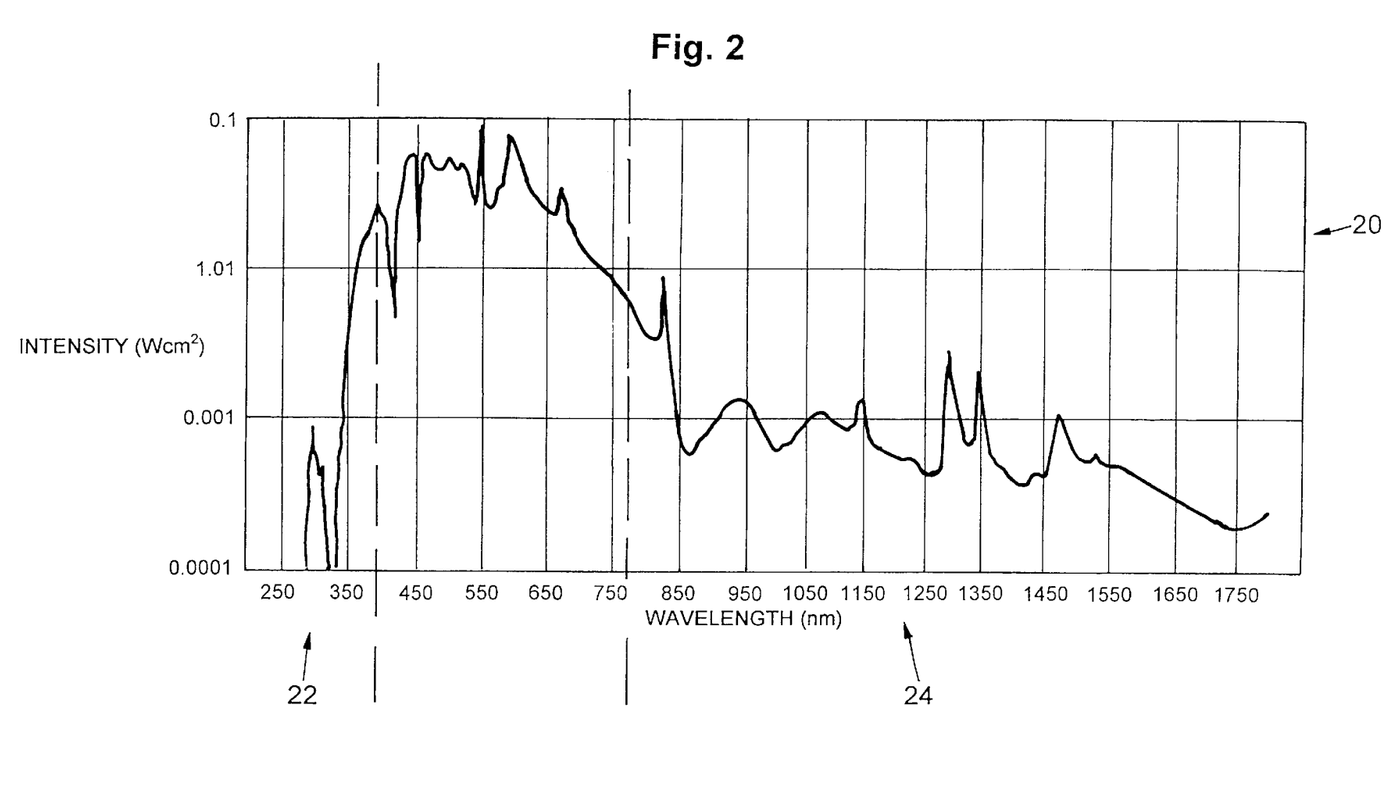
FIG. 2 is a graphic illustration of the spectral distribution of a source of light in accordance with a preferred embodiment of the present invention.

FIG. 2 is a graphic illustration of a spectral distribution 20 of the aforementioned model no. M21E001 metal halide lamp. FIG. 2 shows that the radiant energy produced by this lamp is continuous from about 330 nm to about 1800 nm. That is, there are no gaps or bands in this range where measurable light energy is not emitted. The spectral distribution 20 shows that the lamp generates a fair amount of radiation in both the near ultraviolet (UV) and near infrared (IR) spectrums, 22, 24, respectively.

Both UV and IR radiation can be harmful to the human eye tissue. According to an important aspect of the invention, these components are at least essentially eliminated prior to delivery of the light to a segment of the eye. Referring again to FIG. 1, the filter system 14 comprises a first filter 26 for filtering UV radiation from the generated light and a second filter 28 for filtering IR radiation from the generated light, such that the light filtered by both the first and second filters 26, 28 is at least essentially non-toxic to a human eye. However, in order to maintain the high color temperature (i.e. greater than 3500° K, desirably at least 4500° K or more, and preferably more than 5000° K), the filters 26, 28 do not significantly alter or reduce the color temperature of the generated light. The alteration should be less than twenty percent and preferably less than ten percent.

The UV spectral range includes wavelengths up to between about 360 to 400 nm. There are differing opinions as to the precise lower and upper boundaries of the visible light spectrum. There are also varying opinions as to the lower and upper boundaries of light wavelengths which are toxic to human ocular tissue. The spectral range of visible light wavelengths is from the upper end of the UV range to between about 700 to 760 nm. The IR spectral range of wavelengths extends upward from the upper end of the visible range.

The first, UV filter 26 should filter essentially all of the radiation having a wavelength less than 360 nm. An ultraviolet filter removing 99 percent or more of a light with wavelengths of 375 nm and less has been successfully used. However, under extreme conditions not normally encountered in ordinary ophthalmic use of such light sources, some retinal discoloration was noted. It is believed that 360 nm might be the lowest end of the light spectrum from the preferred light source (or from comparable light sources) that might be safely used within the human eye under at least some circumstances. There has been some concern expressed that even visible blue light near the UV end of the visible light spectrum can be toxic to ocular tissue under certain circumstances or to certain individuals. Therefore, 420 nm is believed to be the lowest end of the visible light spectrum that might be safely used under all circumstances.

A preferred UV filter uses "Schott" filter glass, as is known by those of skill in the art. Such a UV filter is provided by Andover Corp. of Salem, N.H., model no. 420FG03, which is a glass type filter with rated effective ultraviolet reflectance of over 99% of the total light generated by the source of light 12 at wavelengths of 420 nm and below. That is, only one percent or less of the light incident on the filter having wavelengths of 420 nm or less is passed by in the filter. Although a specific model no. and type of UV filter has been disclosed, it will be apparent to those of ordinary skill in the art that other UV filters are suitable for effectively filtering such UV radiation which is harmful to the human eye, which do not significantly alter the color temperature of the generated light.

The second IR filter 28 is used to eliminate light in the infrared spectrum (i.e. at least greater than 760 nm) harmful to ocular tissue. The preferred, second IR filter 28 has an effectiveness of greater than 90% with respect to light in the infrared spectrum and has at least such an effectiveness particularly with respect to wavelengths of at least about 760 nm and up. A suitable IR filter is provided by Andover Corp. of Salem, N.H., model no. 775FW82, which is a hot mirror type IR filter. This device has an average transmittance greater than or equal to 85 percent for light with wavelengths between 450 to 675 nm and an average reflectance of greater than or equal to 90 percent for wavelengths between 750 and at least about 1200 nm. However, as with the first filter 26, it will be apparent to those of ordinary skill in the art that other IR filters are suitable for at least substantially removing from the generated light such IR spectrum component which is toxic to the human eye, without also significantly altering the color temperature of the generated light.

Either separate UV and IR filters can be used or a dual IR/UV filter could be used, such as a glass type UV filter with a laminate or coating thereon for filtering IR radiation. In an alternative embodiment, the first and second filters 26, 28 may comprise a single glass type UV filter with an IR coating having an average transmittance of greater than or equal to 85 percent over 450 to 655 nm and an average reflectance of greater than or equal to 90 percent over wavelengths from 730 to at least 1150 nm with a 50% cut-off at 690±10 nm. Such a filter can be obtained from Optical Corporation of America of Marlborough, Mass. The glass type UV filter passes no more than about one percent of light having a wavelength of 360 nm or less and preferably of light having a wavelength of 420 nm or less. It will be appreciated that such filters may be rated and available at 5, 10 or larger nanometer increments and that all have a transition range of wavelengths.

The first and second filters 26, 28 may be any size or shape. It will be understand by those of ordinary skill in the art that the size and relative positions of the filters 26, 28 with respect to each other is not critical and thus could differ from that shown in FIG. 1.

The preferred filter system 14 further comprises a reflector 30 integrally attached or mounted to the source of light 12. The reflector 30 reflects and focuses the light produced by the source of light 12. It will be noted by those of ordinary skill in the art that the preferred metal halide short arc lamp emits light out of the side of the lamp, and not out of the lamp ends. Therefore light is passed to the filters 26,28 only by virtue of the presence of reflector 30. Lamp 12 and reflector 30 may also be considered to collectively constitute a source which generates light of the present invention like lamp 12 alone.

In the preferred embodiment, the reflector 30 preferably comprises an elliptical reflector, and more preferably, a dichroic elliptical reflector which encompasses 360° of (i.e. fully circumscribes) the light source 12. The reflector 30 both focuses the generated light and filters out about 80% of the infrared radiation of the generated light. The dichroic material of the reflector begins discernable transmission by about 700 nm and transmits at least about 80% or more of the IR spectrum beginning between 800 and 850 nm. Nearly 100% of the UV and visible spectrum below 700 nm is reflected and passed as generated light to filters 26, 28, by reflector 30. By transmitting only about 80% or more of the IR spectrum through the reflector 30 (and out the back of the reflector), only about 20% or less of the total IR spectrum energy is reflected and passed towards the first and second filters 26, 28. Thus, the reflector 30 is, in effect, a first IR filter. Although the second IR filter 28 provides only about 90% IR filtration, the second IR filter 28 is filtering about 20% or less of the total IR light output by lamp 12. That is, since the reflector 30 initially filters out about 80% of the infrared spectrum before the light reaches the second filter 28, the second IR filter only receives about 20% or less of the infrared energy originally generated by the light source 12. Therefore, the second IR filter 28, which filters about 90% of the remaining infrared energy, is adequate to rid the generated light of remaining toxic IR energy. The selected reflector 30 and the second IR filter 28 should collectively pass only about two percent or less of the infrared light above 760 nm originally generated by the source 12, suggestedly only about two percent or less of all infrared light above 720 nm and preferably only about two percent or less of all light above 700 nm. It will further be appreciated that the use of multiple infrared filters can help in dissipating heat created by the light source and that the 80 percent/90 percent filtering effectiveness of reflector 30 and IR filter 28 can be varied and still achieve the desired goal of passing no more than about two percent of the original infrared spectral component of light source 12 through the filters of source 10. Suggestedly, the reflector 30 is selected to remove more than half of the generated infrared light output from lamp 12 and desirably removes a significant portion (e.g. about ⅔ or more) of the infrared component.

Figure 3:
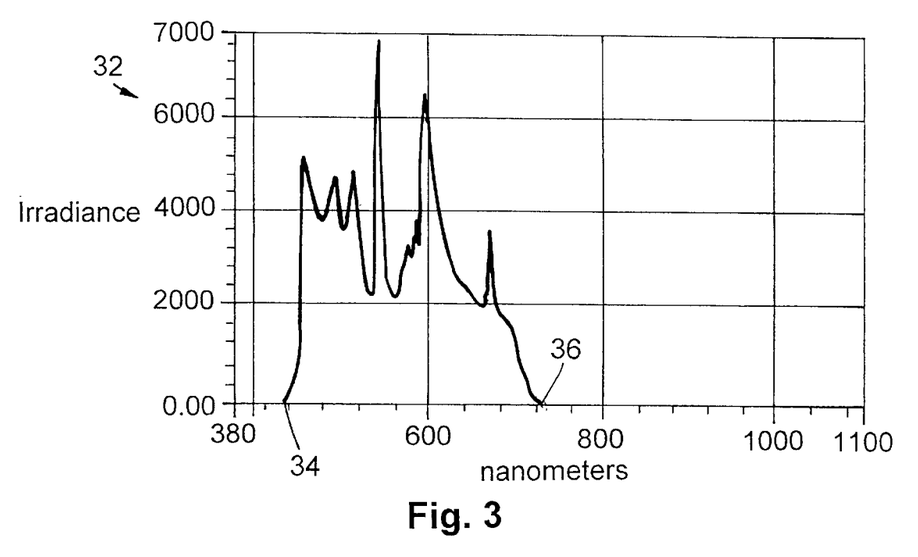
FIG. 3 is a graphic illustration of the spectral distribution of a filtered light in accordance with a preferred embodiment of the present invention.

Referring now to FIG. 3, a graphic illustration 32 of a spectral analysis of the white light source 10 in accordance with the present invention is shown. The graph 32 shows the measure irradiance in microwatts/cm$^2$ verses wavelength of the light delivered by the white light source 10 after the light generated by the source of light 12 is acted upon by the filter system 14. Total irradiance of the source of white light is about 972 milliwatts/cm$^2$ with an index of correlation of 88%. As indicated by the graph 32, the UV and IR spectrums are effectively filtered out. Remaining is visible light in the range from about 420 nm indicated at point 34 to about 720 nm indicated at point 36. This result was achieved using the Andover Corp. UV filter model no. 420FG03 with the Andover Corp. IR filter model no. 775FW82. With the Optical Corporation of America IR coating on the same UV filter glass, point 34 would be shifted down to about 700 nm. In addition, the color temperature of the delivered light is only slightly shifted down (shifted less than 10 percent) by the filter system 14 from about 5830° K to about 5380° K. This temperature is still more than 5000° K and therefore more than halfway between the correlated color temperatures of light sources previously used (e.g. 3200° K) and sunlight (e.g. 6800° K).

Figure 4:
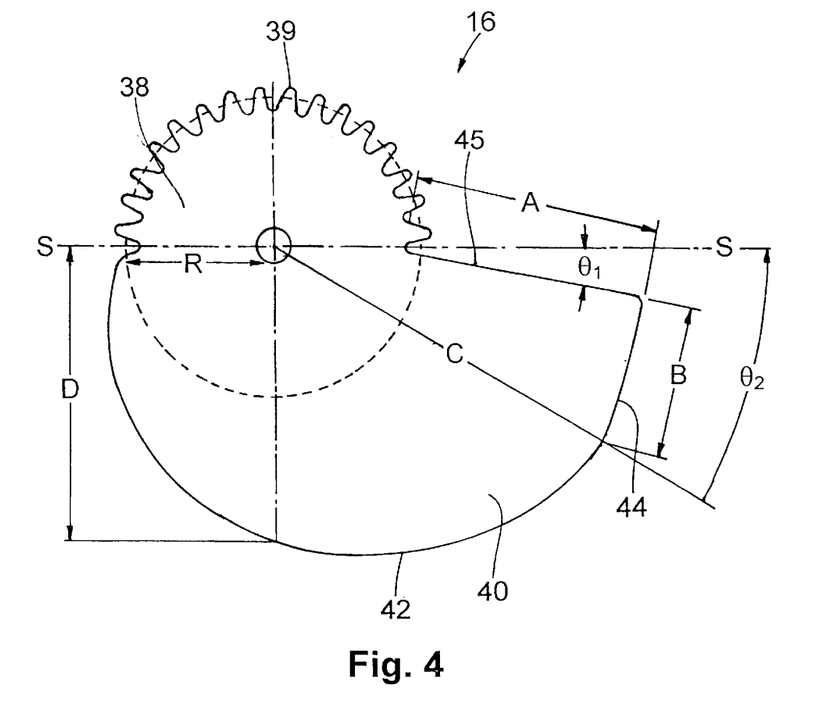
FIG. 4 is an enlarged plan view of a diaphragm in accordance with a preferred embodiment of the present invention.

Referring now to FIG. 4, an enlarged plan view of the diaphragm 16 is shown. The diaphragm 16 is provided to control transmission of the light generated by the source of light 12. The diaphragm 16 is preferably a linear type diaphragm which provides linear control of the light output. In the presently preferred embodiment, the diaphragm 16 comprises a preferably semicircular gear portion 38 with teeth 39 and a linear-helix portion 40 attached to or integral with the gear portion 38. The gear portion 38 extends through a circular arc of about 180°, (i.e., approximately half of one full rotation around the diaphragm), with the linear-helix portion 40 encompassing the remainder of the diaphragm 16. Rotation of the diaphragm 16 introduces a linear section 44 of the linear-helix portion 40 of the diaphragm 16 in front of the source of light 12, to control the amount of light passing the diaphragm 16. A gear connected to a separate shaft (neither shown) controls the rotation of the diaphragm 16, which in turn controls how much of the linear-helix portion 40 is positioned in front of the source of light 12 passing through the path of light from the source 12 through the filters 26, 28. As more of the diaphragm 16 is rotated in front of the source of light 12, less light is allowed to pass by the diaphragm 16.

The diaphragm 16 may be of any size or have any gear configuration, and may be made of any suitable materials, such as stamped metal or a polymeric material. In the presently preferred embodiment, the gear portion 38 of the diaphragm 16 has a radius R of approximately 0.50 inches and a 32 pitch per 20°, with a pitch diameter of 1.0 inch. The linear-helix portion 40 includes a perimeter with an arcuate, section 42, which extends from one end of the gear portion 38 to the linear section 44 of the perimeter, with the linear section 44 being connected to a second end of the gear portion 38 by an edge 45. The linear section 44 has a length B of approximately 0.50 inches. A distance from an outer periphery of the gear 38 to the linear perimeter section 44 is denoted as A, and is preferably approximately 0.84 inches. A distance from a center of the gear portion 38 to an outer periphery of the arcuate section 42, denoted at C, is preferably approximately 1.30 inches and the distance at D is preferably approximately 0.975 inches. The arcuate perimeter section 44 is located at an angle $\theta_1$ from a line S—S, which bisects the gear 38, and extends for an angle $\theta_2$ from the line S—S. Preferably, $\theta_1$ is approximately 10° and $\theta_2$ is approximately 30°.

Figure 5:
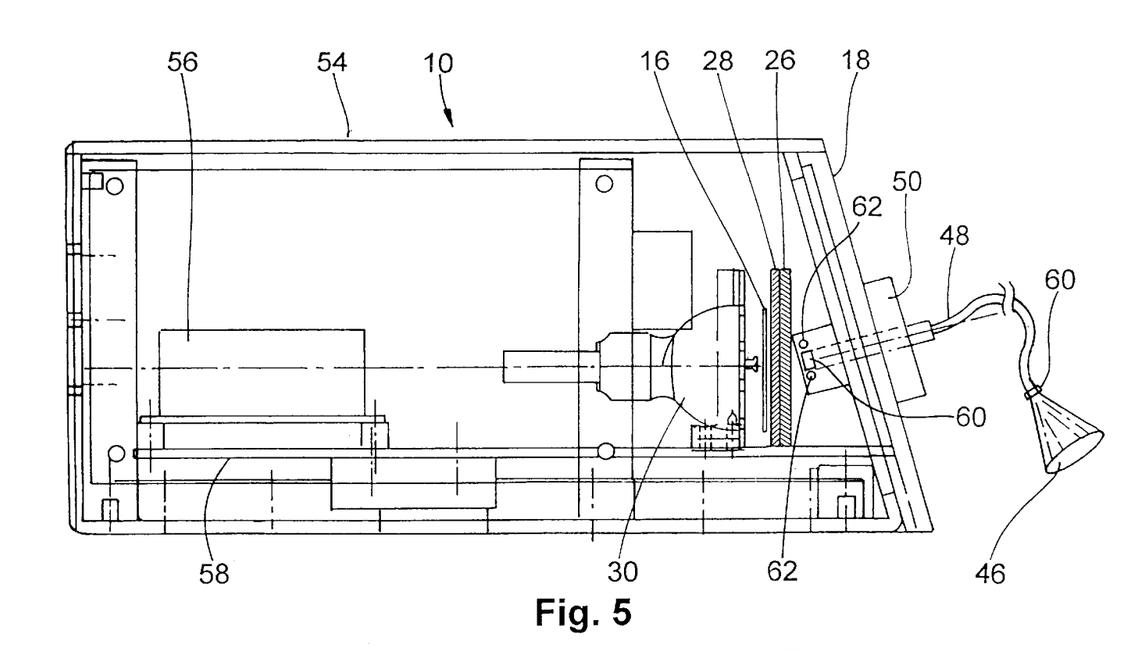
FIG. 5 is a side elevational view, partially in cross-section of the white light source, including a housing, in accordance with the present invention.

Referring now to FIG. 1 and FIG. 5, the front panel 18 facilitates delivery of the filtered light, shown at 46 (FIG. 5), to a work space or area under observation, such as the aforementioned anterior or posterior portion of a human eye. The front panel 18 preferably includes a front panel port assembly 50 for receiving one end, a proximal end, of a fiber optic cable 48. The filtered light 46 passed by the filters 26, 28 is focused on a proximal end of the fiber optic cable 48 such that the fiber optic cable 48 receives the filtered light 46 and delivers the filtered light 46 to the work space. That is, a focal point of the filtered light 46 is focused on the proximal end of the fiber optic cable 48. The fiber optic cable 48 is received within the front panel port 50 of the front panel 18 using a connector. The fiber optic cable 48 may be a plastic cable, which is disposable, such as an "intralux" style of fiber optic cable or adaptor. Such cables and connectors are generally known to those of ordinary skill in the art and further description of such a cable is not necessary for understanding the present invention.

Referring to FIG. 1, the front panel 18 is preferably disposed at an acute angle a with respect to the planes of the first and second filters 26, 28 and face of the light source 12 to facilitate and optimize the light quality and intensity transmitted through the first and second filters 26, 28 to the fiber optic cable 48. In FIG. 1, the angle $\alpha$ is shown with reference to a vertical line V—V parallel to the planes of filters 26, 28 and the face of the reflector 30 of light source 12.

Figure 6A:
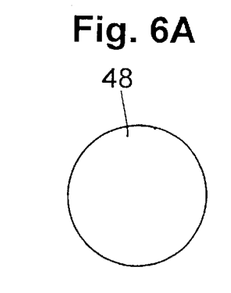
FIG. 6A is a cross-sectional view of a beam of light output from the white light source with a front panel at a 15° angle.
Figure 6B:
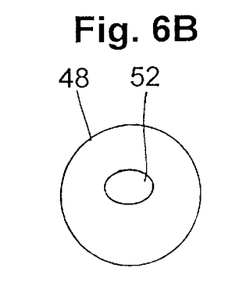
FIG. 6B is a cross-sectional view of a beam of light output from the white light source with a front panel in a vertical orientation.

Referring now to FIGS. 6A and 6B, placing the front panel 18 at an angle homogenizes the light focused on the fiber optic cable 48. FIGS. 6A and 6B show a typical light output with the front panel 18 at an acute, non-zero angle ($\alpha=15°$) and straight on ($\alpha=0°$), respectively. As shown in FIG. 6B, when the front panel 18 is not disposed at an acute angle to the plane(s) of the filter(s) and face of reflector 30 but is positioned at a zero angle, the light introduced to the fiber optic cable 48 includes a darkened region 52. Whereas in FIG. 6A, when the front panel 18 is disposed at an acute, nonzero angle to the plane(s) of the filter(s), the light introduced to the fiber optic cable 48 has a uniform distribution and does not include a darkened region. In the presently preferred embodiment, the acute, non-zero angle $\alpha$ is approximately 15° to the planes of filters 26, 28 and the face of the reflector 30 of light source 12.

Although positioning the front panel 18 at a 15° angle to the plane of the filters 26, 28 eliminates the majority of the problems with halos and/or dark rings (FIG. 6B) at the output of the fiber optic cable 48, there are still instances in which a darkened region is manifested. Accordingly, the present invention further provides a diffuser mechanism 60 (FIG. 5) which alters the light waves of the light output from the source 12 such that the light output of the fiber optic cable 48 is uniformly distributed or homogeneous. In the presently preferred embodiment, the diffuser mechanism 60 comprises a polymeric material positioned between the source 12 and the fiber optic cable 48 through which the light passes. The polymeric material introduces a light loss in the generated light. Alternatively, the diffuser mechanism 60 may be located at a distal end of the fiber optic cable 48, as also indicated in FIG. 5.

In a first operational example, a clear polycarbonate material approximately 0.005 inches thick having a matte and velvet finish was cut to a diameter of about 0.395 inches and positioned within a retaining mechanism 62, such as a retaining ring. A first end of the fiber optic cable 48 was then positioned proximate to the polycarbonate material. Preferably, the end of the fiber optic cable 48 physically butts up to the polycarbonate material. The polycarbonate material introduces between about 1 to about 1.5 candela of light loss. The tighter the fiber optic cable 48 is positioned to the polycarbonate material, the higher the light transmission, such that luminous light output is maximized while dark regions and rings are eliminated. Thus, it is preferred that the polycarbonate material be positioned as close as possible to the fiber optic cable 48. Such polycarbonate material is commercially available from Laird Plastics of Bensenville, Ill.

Although a polycarbonate material is preferred, the same or similar results can be achieved using a polymeric material (not necessarily polycarbonate) which has been finished, such as by sanding or etching, so that the same effect is achieved as with the matte and velvet finish on the aforedescribed polycarbonate material. However, polycarbonate material offers a high resistance to heat, which is an important consideration due to the fact that diffuser mechanism 60 must withstand the heat produced by the source 12. Accordingly, other polymeric materials which also offer a high heat resistance may be acceptable substitutes for the polycarbonate material.

In addition to polymeric materials, other materials which are capable of passing light and withstanding heat may also be used. For instance, glass may be finished, such as by sanding or etching, and disposed within the retaining mechanism 62. The end of the fiber optic cable 48 is then positioned against or proximate to the finished glass. The glass allows the light output to be maximized while eliminating all rings and dark regions. Suitable glass is commercially available from Edmund Scientific Co., part #32947 and may be etched using Armor Etch available from Armor Product of Wyckoff, N.J. Also, a ruby or other form of transparent aluminum oxide may be used.

The diffuser mechanism 60 may alternatively comprise an adhesive material applied to the fibers at an end of the fiber optic cable 48. It has been found that a cured adhesive material applied to the end of the fiber optic cable 48 creates a haze, which similar effects on the light output as the aforedescribed polymeric or glass diffuser means. For example, LocTite Prism Series 406 adhesive, available from Loctite Corp. may be applied to the end of the fiber optic cable 48. Preferably, the curing time of the adhesive is accelerated by slightly warming the adhesive before applying the adhesive to the end of the fiber optic cable 48. Upon completion of the curing process, the adhesive achieves a cloudy haze. However, the process of applying and curing the adhesive must be tightly controlled in order to achieve the desired effect Light output loss has been found to vary between about 1 to about 4 candela.

Furthermore, the polymeric material and the adhesive methods may be combined with the adhesive being disposed between the one end of the fiber optic cable and the polymeric material. Moreover, a similar effect to a combination of the adhesive and polycarbonate material may be achieved using a piece of adhesive tape applied to the end of the fiber optic cable 60.

Yet another manner in which darkened regions and halos may be eliminated is to operate on the fibers of the fiber optic cable 48. It has been found that breaking the cladding of the fibers, and then straightening the fibers achieves the desired result of eliminating darkened regions and halos. That is, the fibers are tightly folded or stretched so that the cladding breaks. The fibers are then straightened so that light transmission is regained. Although similar results as the polymeric and glass methods described above are achieved, this method is less desirable, as is the method comprising the application of adhesive to the fibers, because these methods must be used on every fiber of the fiber optic cable 48. Whereas, the polymeric material/glass method can be incorporated into the light source 10 and accommodates the use of a variety of types of fiber optic cables.

Referring again to FIG. 5, the white light source 10 further comprises a housing 54 in which the source of light 12, the first and second filters 26, 28 and the diaphragm 16 are located. The housing 54 further preferably houses the electronic components, shown at 56, necessary to energize the source of light 12. Such electronic components 56 are generally well known to those of ordinary skill in the art and a detailed description thereof is not necessary for a complete understanding of the present invention. Preferably, the housing 54 interior is accessible to a user for maintenance, such as for changing or replacing a lamp bulb. For instance, the front panel 18 may be hinged and include a latch (not shown), thereby permitting the front panel 18 to be opened. In order to further facilitate access to the interior of the housing 54 and the electronic components 56, the source of light 12, and the first and second filters 26, 28, and other components located within the housing, such components may be located on or secured to a chassis 58 slidably disposed on a rail bearing which allows the chassis 58 to slide out of the housing 54.

As previously discussed, the present invention preferably includes filters 26, 28 for filtering at least essentially all ultraviolet and infrared radiation in the generated light reaching those filters, as such light components are toxic to human ocular tissue. Furthermore, in the presently preferred embodiment, the filters 26, 28 comprise a UV glass substrate with an IR coating. The IR coating filters out all light above 700 nm.

Figure 7:
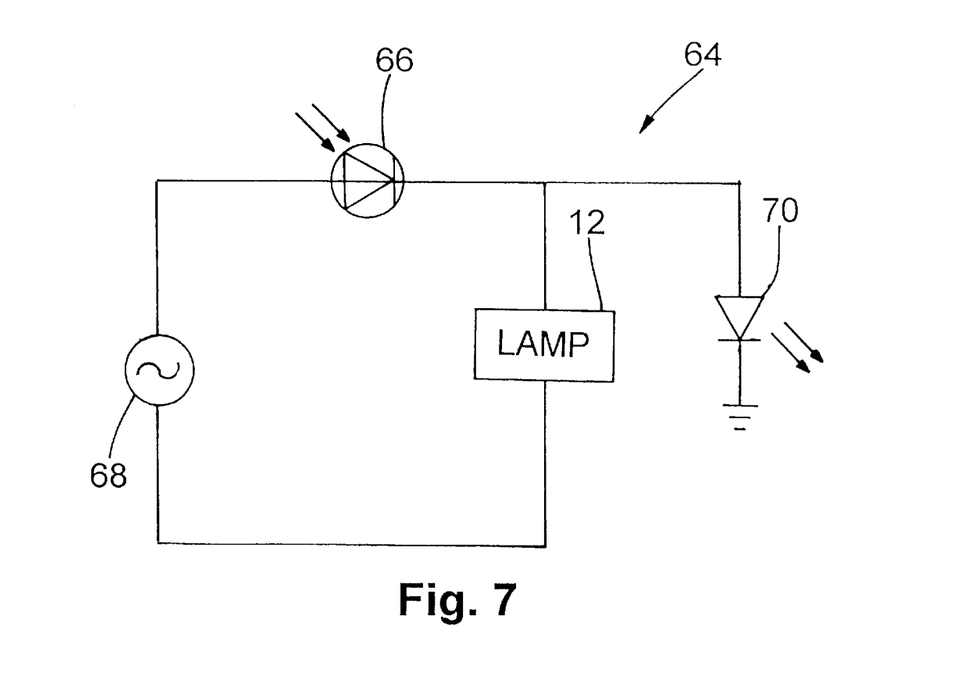
FIG. 7 is an electrical schematic diagram of a circuit for detecting the delivery of toxic radiation.

Referring now to FIG. 7, as a safety measure, the present invention further comprises an electrical circuit 64 for detecting a misplaced, misaligned or damaged IR filter. In the presently preferred embodiment, the electrical circuit 64 comprises a photo diode 66 which detects light at wavelengths above about 880 nanometers. If the UV/IR filter breaks, is misaligned, or otherwise allows IR light to pass thereby such that IR light is allowed to pass to the fiber optic cable 48, such IR light is detected by the photo diode 66. The photo diode 66 is connected to a power source 68 which is used to energize the lamp 12. Once the photo diode 66 detects light above about 880 nm, the diode 66 breaks or opens the electrical connection between the lamp 12 and the power source 68, thereby turning off the lamp 12. The photo diode 66 is further connected to an indicator light 70, such as an LED located on a control panel (not shown) of the light source 10, which signifies a filter problem. Although the electrical circuit 64 detects IR light transmission caused by a misplaced or broken filter, the purpose of the circuit 64 is actually to alert an operator and prevent transmission of harmful UV light. That is, since the IR coating is laminated on the UV glass, the photo diode in effect also detects the transmission of UV radiation caused by a misplaced or broken filter. Of course, it will be understood by those of ordinary skill in the art that other electrical circuit means can be used to detect the transmission of UV radiation and/or IR radiation and prevent the transmission of such harmful radiation.

An ophthalmic artificial light source apparatus has been disclosed for producing white light having a correlated color temperature of greater than 3500° K, and preferably greater than 5000° K. In a preferred embodiment, the light source comprises a metal halide lamp for producing light having a high color temperature and within a predetermined spectral bandwidth and a filter system which eliminates substantially all of the UV and IR radiation emitted by the lamp and which does not substantially reduce the color temperature of the light. The preferred light source delivers light with a color temperature of about 5380° K and filtered of at least essentially all ultraviolet and infrared radiation components toxic to human ocular tissue. The UV and IR spectrums are so completely filtered out that the remaining light is essentially only in the visible spectrum.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A white light source for use by surgeons for illuminating an observation area and providing high clarity and vision thereof, the white light source comprising:

a source generating light having an ultraviolet (UV) spectrum component, an infrared (IR) spectrum component and a substantially continuous spectral distribution of visible light;

a first radiation filter for removing at least essentially all of the UV spectrum component of the generated light toxic to human eye tissue;

a second radiation filter for removing at least substantially all of the IR spectrum component of the generated light toxic to human eye tissue; and means for diffusing the filtered light to facilitate delivering a homogeneous light output.

2. The white light source of claim 1 further comprising a fiber optic cable having a proximal end positioned to receive the diffused, filtered light and deliver the diffused, filtered light to the observation area.

3. The white light source of claim 2 wherein the diffusing means comprises a finished polymeric material positioned proximate to one end of the fiber optic cable.

4. The white light source of claim 3 wherein the finished polymeric material is positioned against the proximal end of the fiber optic cable.

5. The white light source of claim 4 wherein the finished polymeric material is able to withstand heat produced by the light generating source.

6. The white light source of claim 3 wherein the diffusing means further comprises an adhesive applied to fibers at the one end of the fiber optic cable, the adhesive being disposed between the one end of the fiber optic cable and the finished polymeric material.

7. The white light source of claim 3 wherein the finished polymeric material comprises a polycarbonate material having a matte and velvet finish.

8. The white light source of claim 3 wherein the finished polymeric material introduces about a 1 to about 1.5 candela of light loss.

9. The white light source of claim 2 wherein the diffusing means comprises a finished piece of glass positioned proximate to one end of the fiber optic cable.

10. The white light source of claim 9 wherein the glass is finished via etching.

11. The white light source of claim 9 wherein the glass is finished via sanding.

12. The white light source of claim 2 further comprising a retaining mechanism which holds the diffusing means in a fixed position.

13. The white light source of claim 2 wherein the diffusing means comprises an adhesive applied to fibers at one end of the fiber optic cable.

14. The white light source of claim 2 wherein the diffusing means comprises a piece of tape applied to one end of the fiber optic cable.

15. The white light source of claim 2 wherein the diffusing means comprises the fiber optic cable wherein cladding thereof has been broken and then straightened.

16. The white light source of claim 1 further comprising an electrical circuit for detecting toxic radiation not filtered by the first and second filters.

17. The white light source of claim 16 wherein the electrical circuit turns off the light generating source upon detection of the toxic radiation.

18. The white light source of claim 16 wherein the electrical circuit comprises a photo diode electrically connected to a power source of the light generating source.

19. The white light source of claim 18 wherein the electrical circuit further comprises an indicator for indicating detection of the toxic radiation.

20. The white light source of claim 19 wherein the indicator comprises an LED electrically connected to the photo diode.

21. The white light source of claim 1 wherein the first and second filters comprises a glass type UV filter with an IR coating.

22. The white light source of claim 1 wherein the light source comprises a metal halide short arc lamp.

23. A white light source for use by surgeons for illuminating an observation area in a human eye and providing high clarity and vision thereof, the white light source comprising:

a source generating light having an ultraviolet (UV) spectrum component, an infrared (IR) spectrum component and a substantially continuous spectral distribution of visible light and a color temperature greater than 3500° K;

a first radiation filter located to receive the light generated by the source and remove essentially all of the UV spectrum component of the generated light toxic to human eye tissue;

a second radiation filter located to also receive the generated light received by the first radiation filter and remove essentially all of the IR spectrum component of the generated light toxic to human eye tissue, such that the light filtered by the first and second filters is essentially non-toxic to human eye tissue and has a color temperature of greater than 3500° Kelvin; and an electrical circuit for detecting radiation toxic to human eye tissue not filtered by the first and second filters.

24. The white light source of claim 23 wherein the electrical circuit turns off the light generating source upon detection of the toxic radiation.

25. The white light source of claim 24 wherein the electrical circuit comprises a photo diode electrically connected to a power source of the light generating source.

26. The white light source of claim 25 wherein the electrical circuit further comprises an indicator for indicating detection of the toxic radiation.

27. The white light source of claim 26 wherein the indicator comprises an LED electrically connected to the photo diode.

28. A method of providing a white light for illuminating an anterior or posterior segment of an eye and providing high clarity and vision thereof, comprising the steps of:

generating light having a continuous light spectrum and color temperature of greater than 3500° K with a light source;

filtering ultraviolet (UV) radiation from the generated light with a first filter;

filtering infrared (IR) radiation from the generated light with a second filter;

diffusing the filtered light; and delivering the diffused, filtered light to a surgical area, wherein the first and second filters do not substantially change the color temperature of the generated light, and the delivered filtered light is at least essentially non-toxic to human eye tissue, has a color temperature of greater than about 3500° K, and is delivered substantially homogeneous in distribution.

29. The method of claim 28 further comprising the step of detecting the delivery of toxic radiation.

30. The method of claim 29 further comprising the step of turning off the light generation upon detection of the toxic radiation.

* * * * *